(12) United States Patent
Kataoka et al.

(10) Patent No.: US 8,304,497 B2
(45) Date of Patent: Nov. 6, 2012

(54) ELECTROSTATICALLY BONDED POLYMER VESICLE

(75) Inventors: Kazunori Kataoka, Tokyo (JP); Aya Koide, Yokohama (JP); Kensuke Osada, Hasuda (JP); Yuichi Yamasaki, Tokyo-To (JP); Shigeto Fukushima, Narashino (JP); Joon-Sik Park, Tokyo-To (JP)

(73) Assignee: The University of Tokyo, Tokyo-to (JP)

( * ) Notice: Subject to any disclaimer, the term of this patent is extended or adjusted under 35 U.S.C. 154(b) by 1319 days.

(21) Appl. No.: 11/919,744

(22) PCT Filed: Apr. 28, 2006

(86) PCT No.: PCT/JP2006/309008
§ 371 (c)(1),
(2), (4) Date: Nov. 1, 2007

(87) PCT Pub. No.: WO2006/118260
PCT Pub. Date: Nov. 9, 2006

(65) Prior Publication Data
US 2009/0081458 A1    Mar. 26, 2009

(30) Foreign Application Priority Data

May 2, 2005  (JP) .................. 2005-134350

(51) Int. Cl.
*A61K 47/30* (2006.01)
*C08L 77/04* (2006.01)
(52) U.S. Cl. ........ 525/403; 525/409; 525/419; 525/420; 514/772.1; 514/772.3
(58) Field of Classification Search ..... 428/402–402.24; 427/213.3–213.36; 264/4–4.7
See application file for complete search history.

(56) References Cited

U.S. PATENT DOCUMENTS 7,056,532 B1 * 6/2006 Kabanov et al. ............ 424/486
7,780,957 B2 * 8/2010 Kataoka et al. ........... 424/78.17

FOREIGN PATENT DOCUMENTS

| JP | 04-175352 | 6/1992 |
|---|---|---|
| JP | 08-188541 | 7/1996 |
| JP | 2001-131271 | 5/2001 |
| JP | 2001-208754 | 8/2001 |
| JP | 2002-179556 | 6/2002 |
| WO | 99/61512 | 12/1999 |
| WO | WO/2004/099287 | * 11/2004 |

OTHER PUBLICATIONS

Schladd, Helmut, et al. Formation of Amphiphilic Polyion Complex Vesicles from Mixtures of Oppositely Charged Block Ionomers, Macromolecules, vol. 36, No. 5, pp. 1417-1420, Mar. 11, 2003.*
"Spontaneous Formation of Vesicles from Complexes of Block Ionomers and Surfactants" authored by Kabanov et al. and published in JACS (1998) 120(38), 9941-9942.*
"Short-Life Core-Shell Structured Nanoaggregates Formed by the Self-Assembly of PEO-bPAA/ETC (1-(3-Dimethylaminopropyl)-3-ethylcarbodiimide Methiodide) and Their Stabilization" authored by Gu et al. and published in Macromolecules (2004) 27, 1666-1669.*
"Formation of Polyion Complex Micelles in an Aqueous Milieu from a Pair of Oppositely-Charged Block Copolymers with Poly(ethylene glycol) Segments" authored by Harada et al. and published in Macromolecules (1995) 28, 5294-5299.*
"Semipermeable Polymer Vesicles (PICsome) Self-Assembled in Aqueous Medium from a Pair of Oppositely-Charged Block Copolymers: Physiologically Stable Micro/Nanocontainers of Water-Soluble Macromolecules" authored by Koide et al., and published in JACS (2006) 128, 5988-5989.*
Japanese Office Action issued Nov. 29, 2011 in corresponding Japanese Application No. 2007-514840, with English translation thereof.
Supplementary European Search Report issued May 14, 2012 in corresponding European Application No. 06745867.9.
Dennis E. Discher et al., "Polymer Vesicles", Science Magazine, vol. 297, Aug. 2002, pp. 967-973.

* cited by examiner

*Primary Examiner* — Marc Zimmer
(74) *Attorney, Agent, or Firm* — Wenderoth, Lind & Ponack, L.L.P.

(57) ABSTRACT

The present invention discloses a vesicle which is excellent in structure stability and environmental responsiveness and also can be produced by a simple operation. More particularly, the present invention discloses a vesicle comprising a membrane formed of a first block copolymer containing a non-chargeable hydrophilic segment and a chargeable segment, and a second block copolymer containing a non-chargeable hydrophilic segment and a chargeable segment having an electric charge which is opposite to that of the chargeable segment of the first block copolymer.

21 Claims, 5 Drawing Sheets

ELECTROSTATICALLY BONDED POLYMER VESICLE

BACKGROUND OF THE INVENTION

1. Field of the Invention

The present invention relates to a vesicle which is formed of a water-soluble and chargeable block copolymer and, more particularly, to a vesicle which has a useful function as a drug delivery system and various materials.

2. Background Art

It is known that a polymer having a precisely controlled primary structure can be spontaneously organized to form a higher order structure. Specific examples thereof include structures such as micells and vesicles. Such a structure formed by self-organization of a polymer can be subjected to various molecular designs and can be a structure having a novel function in addition to original properties of the polymer. It has hitherto been studied to utilize the structure formed of a self-organized polymer in various fields such as drug delivery systems and materials science.

For example, in Japanese Unexamined Patent Publication (Kokai) No. 8-188541, a part of the inventors of the present invention discloses an electrostatically bonded polymer micell as drug carrier comprising a block copolymer containing a non-chargeable segment and a chargeable segment.

Also, Helmut Schlaad et al., Macromolecules volume 36, number 5, p 1417-1420 discloses that a vesicle referred to as a polymersome can be formed using a block copolymer comprising a poly(1,2-butadiene) block and a poly(cesium methacrylate) block, and a block copolymer comprising a polystyrene block and a poly(1-methyl-4-vinylpyridium iodide) block.

Regardless of expectation of excellent availability, it is often required for the structure formed of a polymer material to use an organic solvent such as chloroform upon production. Furthermore, in the production of a self-organized structure formed of polymers, a complicated operation including several steps is sometimes required. Therefore, it is required to create a structure which has availability and also can be produced by a simple operation.

SUMMARY OF THE INVENTION

The present inventors have now found that a novel vesicle having excellent structure stability and environmental responsiveness can be obtained using two block copolymers having specific structures. Also, the present inventors have found that a novel vesicle can be easily produced by mixing two block copolymers in an aqueous solution. The present invention has been made based on these findings.

Accordingly, an object of the present invention is to provide a novel vesicle.

The vesicle according to the present invention comprises a membrane which is formed of a first block copolymer containing a non-chargeable hydrophilic segment and a chargeable segment, and a second block copolymer containing a non-chargeable hydrophilic segment and a chargeable segment having an electric charge which is opposite to that of the chargeable segment in the first block copolymer.

Since there is no necessity to use an organic solvent in the production of the vesicle according to the present invention, the vesicle can be advantageously utilized in the biomaterial field and DDS. Also, the vesicle according to the present invention contains a center void capable of including a large amount of a compound therein and can be advantageously used as a delivery carrier of a substance in the body and a drug, and fine reactor particles in which a center void serves as a reaction field of an enzyme. Furthermore, the vesicle according to the present invention can stably hold the structure thereof in the presence of saline and serum, and also can impart various functions such as semi-permeability to the membrane thereof. Therefore, the vesicle according to the present invention can be advantageously utilized as a biomaterial or a drug delivery system, which is excellent in structure stability and environmental responsiveness.

DETAILED DESCRIPTION OF THE INVENTION

In this disclosure, the term "vesicle" means the one having a basic structure which contains voids therein and is closed by a membrane.

In this disclosure, unless otherwise specified, the term "alkyl" or "alkoxy" as a group or a portion of the group means that the group is a straight-chain, branched or cyclic alkyl or alkoxy. Also, "$C_{1-12}$" in the case of a "$C_{1-12}$ alkyl group" means that the alkyl group has 1 to 12 carbon atoms.

In this disclosure, unless otherwise specified, the term "aryl" means phenyl, naphthyl, anthnyl, or pyrenyl.

In this disclosure, the term "halogen" means fluorine, chlorine, bromine, or iodine.

In this disclosure, the expression the alkyl group "may be substituted," means that one or more hydrogen atoms on the alkyl group may be substituted with one or more substituents (which may be the same or different). It is apparent to those skilled in the art to decide the maximum number of substituents depending on the number of substitutable hydrogen on the alkyl. Substituents as used herein are selected from the group consisting of halogen, aryl, hydroxyl, amino, carboxyl, cyano, formyl, dimethylacetalized formyl, diethylacetalized formyl, $C_{1-6}$ alkoxycarbonyl, $C_{2-7}$ acylamide, tri $C_{1-6}$ alkylsiloxy (wherein each $C_{1-6}$ alkyl may be the same or different), siloxy, and silylamino.

Vesicle

One feature of the vesicle according to the present invention is that it includes a membrane formed by the interaction of two water-soluble and chargeable block copolymers. Of the two block copolymers which form the membrane of the vesicle, the first block copolymer contains a non-chargeable hydrophilic segment and a chargeable segment, while the second block copolymer contains a non-chargeable hydrophilic segment and a chargeable segment charged to an electric charge which is opposite to that of the chargeable segment in the first block copolymer.

Figure 1:
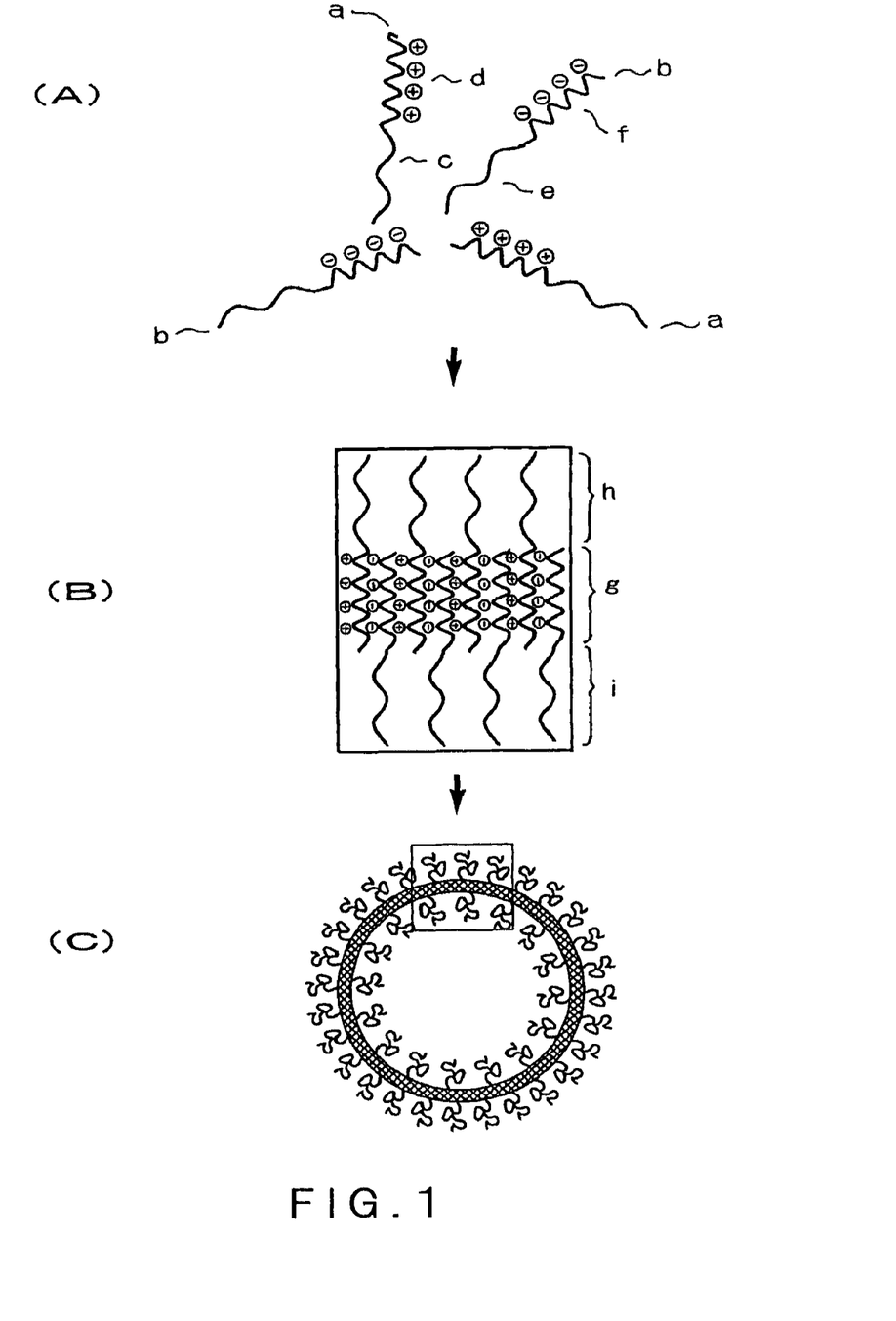
FIG. 1 is a schematic view showing a structure of a vesicle formed of a positively charged block copolymer and a negatively charged block copolymer, and a mechanism of formation of the vesicle.

FIG. 1 is a schematic view showing, as one aspect, a structure of a vesicle according to the present invention and a mechanism of formation of the vesicle.

In FIG. 1A, a first block copolymer (a) contains a non-chargeable hydrophilic segment (c) and a chargeable segment having positive charge (d), while a second block copolymer (b) contains a non-chargeable hydrophilic segment (e) and a chargeable segment having negative charge (f). When the first block copolymer (a) and the second block copolymer (b) are placed in a system in which interaction between electric charges arise, these block copolymers are self-assembled. Therefore, as shown in FIG. 1B, an intermediate layer (g) of an ion complex formed of chargeable segments (d, f) and two hydrophilic layers (h, i) formed of non-chargeable hydrophilic segments (c, e) are formed and a vesicle (C) comprising this structure (B) as a membrane is produced.

As described above, the vesicle according to the present invention is formed by electrostatic interaction between chargeable segments as a main driving force.

Therefore, the formation or dissociation of a vesicle can be controlled by ionic intensity. As a result, the vesicle according to the present invention can exert excellent environmental responsiveness.

As shown in FIG. 1C, the membrane of the vesicle has a three-layered structure comprising an outer layer (h), an intermediate layer (g), and an inner layer (i). According to a preferred aspect of the present invention, the non-chargeable hydrophilic segment in either one of the first block copolymer and the second block copolymer forms an outer layer, while the non-chargeable hydrophilic segment of the other block copolymer, which does not form the outer layer, forms an inner layer.

Also, since the vesicle according to the present invention includes an inner layer formed of the non-chargeable hydrophilic segment, the vesicle can contain an aqueous medium in the center void.

The vesicle according to the present invention is usually in a spherical form. The particle size of the vesicle according to the present invention is not specifically limited so long as it has a hollow structure, but is preferably 10 µm or less, and more preferably from 50 nm to 10 µm.

Chargeable Segment

The chargeable segment contained in the first block copolymer and the chargeable segment contained in the second block copolymer can be charged to mutually opposite electric charges. These chargeable segments are usually formed of a polymer block. The same chain length and charge number of these chargeable segments is advantageous in view of stability of the structure and size of the vesicle, and security of uniformity. Therefore, the chain length and charge number of the chargeable segment in the two copolymers are preferably the same. Specifically, when each of the chargeable segment contained in the first block copolymer and the chargeable segment contained in the second block copolymer is a polymer block formed of a repeating unit containing a monovalent electric charge, the ratio of the number of repeating units in the chargeable segment contained in the first block copolymer to the number of repeating units in the chargeable segment contained in the block copolymer is preferably 1:1. The repeating unit and the charge number in the chargeable segment can be adjusted by appropriately selecting the monomer constituting the chargeable segment, and reaction conditions in case of producing the chargeable segment.

In the present invention, when polyamine is used as the chargeable segment positively charged, the polyamine is positively charged by acid addition thereto. The kind of acid to be added is appropriately decided according to use of the vesicle, and so on.

According to a preferred aspect of the present invention, the chargeable segment which is able to be positively charged of the first or second block copolymer is represented by formula (I) shown below:

[Chemical formula 1]

(I)

wherein $R_1$ represents a —$(CH_2)_3NH_2$ or —$CONH(CH_2)_s$—X, s representing 0 to 20, wherein X represents at least one selected from the group consisting of —$NH_2$, pyridyl, morpholyl, 1-imidazolyl, piperazinyl, 4-($C_{1-6}$ alkyl)-piperazinyl, 4-(amino $C_{1-6}$ alkyl)-piperazinyl, pyrrolidin-1-yl, N-methyl-N-phenylamino, piperidinyl, diisopropylamino, dimethylamino, diethylamino, —$(CH_2)_tNH_2$, and —$(NR_9(CH_2)_o)_p$ $NHR_{10}$ wherein $R_9$ represents hydrogen or methyl, $R_{10}$ represents hydrogen, acetyl, trifluoroacetyl, benzyloxycarbonyl, or tert-butoxycarbonyl, and o represents 1 to 5, p represents 1 to 5, and t represents 0 to 15;

$R_2$ represents hydrogen, acetyl, trifluoroacetyl, acryloyl, or methacryloyl;

a represents 0 to 5,000;

b represents 0 to 5,000; and a+b represents 2 to 5,000.

In formula (1) shown above, when $R_1$ represents —CONH $(CH_2)_s$—X, X may be the same or different functional group for every repeating unit of a chargeable segment.

Furthermore, according to a more preferred aspect of the present invention, in formula (I) shown above, $R_1$ represents —$CONH(CH_2)_s$—$NH_2$ and s represents 2 to 5, $R_2$ represents hydrogen, and a represents 0 to 200, b represents 0 to 200, and a+b represents 10 to 200.

Furthermore, according to a preferred aspect of the present invention, the negatively chargeable segment of the first or second block copolymer is represented by formula (II) shown below:

[Chemical formula 2]

(II)

wherein $R_2$ represents hydrogen, acetyl, trifluoroacetyl, acryloyl, or methacryloyl, each $R_3$ independently represents methylene or ethylene, and c represents 0 to 5,000, d represents 0 to 5,000, and c+d represents 2 to 5,000.

In formula (II) shown above, $R_3$ may be the same or different functional group for every repeating unit of a chargeable segment.

Furthermore, according to a more preferred aspect of the present invention, in formula (II) shown above, $R_2$ represents hydrogen, $R_3$ represents methylene, c represents 0 to 200, d represents 0 to 200, and c+d represents 10 to 200.

Non-Chargeable Hydrophilic Segment

Examples of the non-chargeable hydrophilic segment included in the block copolymers include polyalkylene glycols such as polyethylene glycol, poly(2-isopropyl-2-oxazoline), polysaccharide, polyvinyl alcohol, polyvinyl pyrrolidone, polyacrylamide, polymethacrylamide, polyacrylate ester, polymethacrylate ester, and derivatives thereof. When the block copolymers contain the non-chargeable hydrophilic fragment, the block copolymers stably exist in an aqueous solution without being associated or precipitated, and can efficiently construct a vesicle. Furthermore, by constructing with the block copolymers containing the non-chargeable hydrophilic fragment, the vesicle can hold a stable structure in an aqueous solution.

According to a preferred aspect of the present invention, the non-chargeable hydrophilic segment in the first block copolymer and the non-chargeable hydrophilic segment in the second block copolymer are polyethylene glycol and/or poly(2-isopropyl-2-oxazoline). Furthermore, according to a more preferred aspect of the present invention, the non-chargeable hydrophilic segment in the first block copolymer or the non-chargeable hydrophilic segment in the second block copolymer is polyethylene glycol. Use of polyethylene glycol as the non-chargeable hydrophilic segment is advantageous so as to impart biocompatibility to the vesicle. Also, according to another more preferred aspect of the present invention, the non-chargeable hydrophilic segment in the first block copolymer or the non-chargeable hydrophilic segment in the second block copolymer is poly(2-isopropyl-2-oxazoline). Use of poly(2-isopropyl-2-oxazoline) as the non-chargeable hydrophilic segment is advantageous so as to impart temperature responsiveness to the vesicle.

When polyethylene glycol is used as the non-chargeable hydrophilic segment, the molecular weight (Mw) of polyethylene glycol is preferably from 500 to 15,000, and more preferably from 1,000 to 5,000. Also, when poly(2-isopropyl-2-oxazoline) is used as the non-chargeable hydrophilic segment, the molecular weight (Mw) of poly(2-isopropyl-2-oxazoline) is preferably from 1,000 to 30,000, and more preferably from 1,000 to 10,000. Use of the polymer having the above molecular weight as the non-chargeable hydrophilic segment is advantageous to form a vesicle by the block copolymer prior to formation of a micell.

Block Copolymer

According to a preferred aspect of the present invention, the block copolymer containing a chargeable segment which is able to be positively charged is represented by formula (III) shown below:

[Chemical formula 3]

(III)

wherein $R_1$ represents —$(CH_2)_3NH_2$ or —$CONH(CH_2)_s$—X, s representing 0 to 20, wherein X represents at least one selected from the group consisting of —$NH_2$, pyridyl, morpholyl, piperazinyl, 1-imidazolyl, 4-($C_{1-6}$ alkyl)-piperazinyl, 4-(amino $C_{1-6}$ alkyl)-piperazinyl, pyrrolidin-1-yl, N-methyl-N-phenylamino, piperidinyl, diisopropylamino, dimethylamino, diethylamino, —$(CH_2)_tNH_2$, and —$(NR_9(CH_2)_o)_p$ $NHR_{10}$ wherein $R_9$ represents hydrogen or methyl, $R_{10}$ represents hydrogen, acetyl, trifluoroacetyl, benzyloxycarbonyl, or tert-butoxycarbonyl, and o represents 1 to 5, p represents 1 to 5, and t represents 0 to 15;

$R_2$ represents hydrogen, acetyl, trifluoroacetyl, acryloyl, or methacryloyl;

$R_4$ represents hydrogen, or straight-chain or branched $C_{1-12}$ alkyl which may be substituted;

$R_5$ represents —$(CH_2)_gNH$— and g represents 0 to 5;

a represents 0 to 5,000, b represents 0 to 5,000, and a+b represents 2 to 5,000; and e represents 5 to 2,500.

In formula (III) shown above, when $R_1$ represents —$CONH(CH_2)_s$—X, X may be the same or different functional group for every repeating unit of a block copolymer.

Also, according to a more preferred aspect of the present invention, in formula (III) shown above, $R_1$ represents a —$CONH(CH_2)_s$—$NH_2$ group and s represents 2 to 5, $R_2$ represents hydrogen, $R_4$ represents methyl, and a represents 0 to 200, b represents 0 to 200, and a+b represents 10 to 200, and e represents 10 to 300.

Also, according to another preferred aspect of the present invention, the block copolymer containing a chargeable segment which is able to be positively charged is represented by formula (IV) shown below:

[Chemical formula 4]

(IV)

wherein $R_1$ represents —$(CH_2)_3NH_2$ or —$CONH(CH_2)_s$—X, s representing 0 to 20, wherein X is at least one selected from the group consisting of —$NH_2$, pyridyl, morpholyl, 1-imidazolyl, piperazinyl, 4-($C_{1-6}$ alkyl)-piperazinyl, 4-(amino $C_{1-6}$ alkyl)-piperazinyl, pyrrolidin-1-yl, N-methyl-N-phenylamino, piperidinyl, diisopropylamino, dimethylamino, diethylamino, —$(CH_2)_tNH_2$, and —$(NR_9(CH_2)_o)_pNHR_{10}$ wherein $R_9$ represents hydrogen or methyl, $R_{10}$ represents hydrogen, acetyl, trifluoroacetyl, benzyloxycarbonyl, or tert-butoxycarbonyl, and o represents 1 to 5, p represents 1 to 5, and t represents 0 to 15;

$R_2$ represents hydrogen, acetyl, trifluoroacetyl, acryloyl, or methacryloyl;

$R_6$ represents hydrogen, or straight-chain or branched $C_{1-12}$ alkyl which may be substituted;

$R_7$ represents —$(CH_2)_hNH$— and h represents 0 to 5;

$R_8$ represents straight-chain or branched $C_{1-12}$ alkyl;

a represents 0 to 5,000, b represents 0 to 5,000 and a+b represents 2 to 5,000; and f represents 5 to 2,500.

In formula (IV) shown above, when $R_1$ represents —CONH$(CH_2)_n$—X, X may be the same or different functional group for every repeating unit of a block copolymer.

Also, according to another preferred aspect of the present invention, in formula (IV) shown above, $R_1$ represents —$(CH_2)_3NH_2$, $R_2$ represents hydrogen, $R_6$ represents methyl, $R_8$ represents —$CH(CH_3)_2$, and a represents 0 to 200, b represents 0 to 200, and a+b represents 10 to 200, and f represents 10 to 300.

Also, according to a preferred aspect of the present invention, the block copolymer containing a chargeable segment which is able to be negatively charged is represented by the following formula (V):

[Chemical formula 5]

$$R_4\text{-}(\text{OCH}_2\text{CH}_2)_f\text{-}R_5\text{-}(\text{COCHNH}_2)_a\text{-}(\text{COR}_3\text{CHNH})_d\text{-}R_2$$
with side chains: $R_3$, CO, OH on one branch; CO, OH on the other (V)

wherein $R_2$ represents hydrogen, acetyl, trifluoroacetyl, acryloyl, or methacryloyl;

each $R_3$ independently represents methylene or ethylene;

$R_4$ represents hydrogen, or straight-chain or branched $C_{1-12}$ alkyl group which may be substituted, $R_5$ represents —$(CH_2)_gNH$— and g represents 0 to 5, c represents 0 to 5,000, d represents 0 to 5,000 and c+d represents 2 to 5,000, and i represents 5 to 2,500.

In formula (IV) shown above, $R_3$ may be the same or different functional group for every repeating unit of a block copolymer.

Also, according to another more preferred aspect of the present invention, in formula (V) shown above, $R_2$ represents hydrogen, $R_3$ represents methylene, $R_4$ represents methyl, and c represents 0 to 200, d represents 0 to 200, and c+d represents 10 to 200, and i represents 10 to 300.

Also, according to another preferred aspect of the present invention, the block copolymer containing a chargeable segment which is able to be negatively charged is represented by formula (VI) shown below:

[Chemical formula 7]

$$R_6\text{-}(\text{NCH}_2\text{CH}_2)_j\text{-}R_7\text{-}(\text{COCHNH})_c\text{-}(\text{COR}_3\text{CHNH})_d\text{-}R_2$$
with side chains: CO, $R_8$ on one branch; $R_3$, CO, OH on middle; CO, OH on other (VI)

wherein $R_2$ represents hydrogen, acetyl, trifluoroacetyl, acryloyl, or methacryloyl;

each $R_3$ independently represents methylene or ethylene;

$R_6$ represents hydrogen, or straight-chain or branched $C_{1-12}$ alkyl which may be substituted;

$R_7$ represents —$(CH_2)_hNH$— and h represents 0 to 5, $R_8$ represents a straight-chain or branched $C_{1-12}$ alkyl group;

c represents 0 to 5,000, d represents 0 to 5,000 and c+d represents 2 to 5,000; and j represents 5 to 2,500.

In formula (VI) shown above, $R_3$ may be the same or different functional group for every repeating unit of a block copolymer.

Also, according to another preferred aspect of the present invention, in formula (VI) shown above, $R_2$ represents hydrogen, $R_3$ represents methylene, $R_6$ represents methyl, $R_8$ represents —$CH(CH_3)_2$, c+d represents 10 to 200, and j represents 10 to 300.

Combination of First Block Copolymer and Second Block Copolymer

According to a preferred aspect of the present invention, the first block copolymer contains the non-chargeable hydrophilic segment formed of polyethylene glycol or poly(2-isopropyl-2-oxazoline) and the chargeable segment represented by formula (I) shown above, while the second block copolymer contains the non-chargeable hydrophilic segment formed of polyethylene glycol or poly(2-isopropyl-2-oxazoline) and the chargeable segment represented by formula (II) shown above.

According to more preferred aspect of the present invention, in formula (I) shown above, $R_1$ represents —CONH$(CH_2)_s$—$NH_2$ and s represents 2 to 5, $R_2$ represents hydrogen, and a represents 0 to 200, b represents 0 to 200, and a+b represents 10 to 200 and, in formula (II) shown above, $R_2$ represents hydrogen, $R_3$ represents methylene, and c represents 0 to 200, d represents 0 to 200, and c+d represents 10 to 200.

Also, according to another preferred aspect of the present invention, the first block copolymer is the block copolymer represented by formula (III) shown above, and the second block copolymer is the block copolymer represented by formula (V) shown above.

Also, according to another more preferred aspect of the present invention, in the block copolymer represented by formula (III) shown above, $R_1$ represents —CONH$(CH_2)_s$—$NH_2$ and s represents 2 to 5, $R_2$ represents hydrogen, $R_3$ represents methyl, and a represents 0 to 200, b represents 0 to 200 and a+b represents 10 to 200, e represents 10 to 300 and, in formula (V) shown above, $R_2$ and $R_4$ are as defined above, $R_3$ represents methylene, and c represents 0 to 200, d represents 0 to 200, and c+d represents 10 to 200, and i represents 10 to 300.

Also, according to another preferred aspect of the present invention, the first block copolymer is the block copolymer represented by formula (IV) shown above, and the second block copolymer is the block copolymer represented by formula (V) shown above.

According to another more preferred aspect of the present invention, in formula (IV) shown above, $R_1$ represents —$(CH_2)_3NH_2$, $R_2$ represents hydrogen, $R_6$ represents methyl, $R_8$ represents —$CH(CH_3)_2$, and a represents 0 to 200, b represents 0 to 200 and a+b represents 10 to 200, f represents 10 to 300 and, in formula (V) shown above, $R_2$ is as defined above, $R_3$ represents methylene, $R_4$ represents methyl, and c represents 0 to 200, d represents 0 to 200, and c+d represents 10 to 200, and i represents 10 to 300.

Also, according to another preferred aspect of the present invention, the first block copolymer is the block copolymer represented by formula (III) shown above, and the second block copolymer is the block copolymer represented by formula (VI) shown above.

Also, according to another more preferred aspect of the present invention, in formula (III) shown above, $R_1$ represents —$CONH(CH_2)_s$—$NH_2$ and s represents 2 to 5, $R_2$ represents hydrogen, $R_4$ represents methyl, and a represents 0 to 200, b represents 0 to 200, and a+b represents 10 to 200, e represents 10 to 300 and, in formula (VI) shown above, $R_2$ is as defined above, $R_3$ represents methylene, $R_6$ represents methyl, $R_8$ represents —$CH(CH_3)_2$, and c represents 0 to 200, d represents 0 to 200, and c+d represents 10 to 200, and j represents 10 to 300.

Also, according to another preferred aspect of the present invention, the first block copolymer is the block copolymer represented by formula (IV) shown above, and the second block copolymer is the block copolymer represented by formula (VI) shown above.

Also, according to another more preferred aspect of the present invention, in formula (IV) shown above, $R_1$ represents —$(CH_2)_3NH_2$, $R_2$ represents hydrogen, $R_6$ represents methyl, $R_8$ represents —$CH(CH_3)_2$, and a represents 0 to 200, b represents 0 to 200, and a+b represents 10 to 200, f represents 10 to 300 and, in formula (VI) shown above, $R_2$, $R_6$ and $R_8$ are as defined above, $R_3$ represents methylene, and c represents 0 to 200, d represents 0 to 200, and c+d represents 10 to 200, and j represents 10 to 300.

Utilization of Vesicle

The vesicle according to the present invention can include a compound in the center void. The vesicle according to the present invention can also insert a compound into the membrane thereof. The compound can be appropriately selected according to use and properties of the vesicle and includes, for example, drugs, proteins, fluorescent dyes, nucleic acids, and fine particles.

Production Method

Synthesis of Block Copolymer (1)

As an example of a method for producing a block copolymer of the present invention, a method for producing a polyethylene glycol-poly($\alpha,\beta$-aspartic acid) block copolymer (VIII) as a negatively chargeable block copolymer, and an aminated compound (IX) of a polyethylene glycol-polyaspartic acid block copolymer as a positively chargeable block copolymer in Scheme A will now be described.

Scheme A

[Chemical formula 7]

Polyethylene Glycol-Poly(α,β-Aspartic Acid) Block Copolymer (VIII)

First, the polyethylene glycol-poly(α,β-aspartic acid) block copolymer as the negatively chargeable block copolymer will be described.

β-benzyl-L-aspartate-N-carboxylic anhydride is polymerized using polyethylene glycol having a one-terminal primary amino group as an initiator. Then, the resulting polyethylene glycol-poly-β-benzyl-aspartate copolymer (VII) is debenzylated by an alkali treatment to obtain the polyethylene glycol-poly(α,β-aspartic acid) block copolymer (VIII).

Aminated Compound (IX) of Polyethylene Glycol-Polyaspartic Acid Block Copolymer

Next, the aminated compound (IX) of the polyethylene glycol-polyaspartic acid block copolymer as the positively chargeable block copolymer will be described. The polyethylene glycol-poly-α-benzyl-aspartate copolymer (VII) in Scheme A is reacted with an amine represented by $_2NH-R-NH_2$ (wherein R is $-(CH_2)_{2-5}-$) in a solvent such as DMF, followed by acid addition using HCl to obtain the aminated compound (IX) of a polyethylene glycol-polyaspartic acid block copolymer.

The technique described above easily enables chain length and charge number of the negatively charged poly(α,β-aspartic acid) block in the block copolymer (VIII) to be the same as those of the positively charged (aminated polyaspartic acid) block in the block polymer (IX). Therefore, the technique is advantageous to efficiently produce a homogeneous vesicle.

Synthesis of Block Copolymer (2)

Also, a method for producing a poly(2-isopropyl-2-oxazoline)-poly(α,β-aspartic acid) block copolymer (XI) as a negatively chargeable block copolymer and a poly(2-isopropyl-2-oxazoline)-poly(L-lysine) block copolymer (XIII) as a positively chargeable block copolymer, as another example of the block copolymers in the present invention, will be described.

Poly(2-Isopropyl-2-Oxazoline)-Poly(α,β-Aspartic acid) Block Copolymer (XI)

First, the poly(2-isopropyl-2-oxazoline)-poly(α,β-aspartic acid) block copolymer as the negatively charged block copolymer will be described with reference to Scheme B.

Scheme B

First, 3-benzyl-L-aspartate-N-carboxylic anhydride is produced using poly(2-isopropyl-2-oxazoline) having a one-terminal primary amino group as an initiator. Then, the resulting poly(2-isopropyl-2-oxazoline)-poly-β-benzyl-aspartate copolymer (X) is debenzylated by an alkali treatment to obtain the poly(2-isopropyl-2-oxazoline)-poly (α,β-aspartic acid) block copolymer (XI).

Poly(2-Isopropyl-2-Oxazoline)-Poly(L-Lysine) Block Copolymer (XII)

Also, a poly(2-isopropyl-2-oxazoline)-poly(L-lysine) block copolymer as the positively charged block copolymer will be described with reference to Scheme C.

Scheme C

[Chemical formula 9]

First, ε(benzyloxycarbonyl)-L-lysine-N-carboxylic anhydride is polymerized using poly(2-isopropyl-2-oxazoline) having a one-terminal primary amino group as an initiator. The resulting poly(2-isopropyl-2-oxazoline)-poly(ε-carbobenzoxy-L-lysine) block copolymer (XII) is subjected to a deprotection reaction using an acid to obtain a poly(2-isopropyl-2-oxazoline)-polylysine block copolymer (XIII).

Production of Vesicle

Since the vesicle according to the present invention can be formed by utilizing an electrostatic interaction between block copolymers, it can be easily produced by mixing a first block copolymer and a second block copolymer in an aqueous solution. Furthermore, according to the method of the present invention, the vesicle can be produced without using an organic solvent and therefore the vesicle can be advantageously utilized in the biomaterial field and DDS.

In the production of the present invention, first, a first aqueous solution containing the first block copolymer and a second aqueous solution containing the second block copolymer are prepared. Herein, the first and second aqueous solutions may be purified by filtration, if necessary.

The ratio of the total charge number of the first block copolymer in the first aqueous solution to the total charge number of the second block copolymer in the second aqueous solution is preferably from 5:1 to 1:5, and more preferably about 1:1. The total charge number in the block copolymer is appropriately decided by those skilled in the art according to the number of repeating units which form a chargeable segment in a block copolymer, and the charge number of the repeating units. The use of two block copolymers in the above ratio is advantageous so as to efficiently produce a homogeneous vesicle.

The concentration of the first block copolymer in the first aqueous solution and that of the second block copolymer in the second aqueous solution are appropriately decided taking account of the ratio of the total charge number between the block copolymers, solubility of the block copolymer in the aqueous solution, and formation efficiency of the vesicle.

Since any of the block copolymers are water-soluble, the solvent in the first and second aqueous solutions is preferably water or a buffer, and more preferably a 10 mM Tris/HCl buffer.

The pH in the first and second aqueous solutions may be appropriately adjusted so long as an adverse affect is not exerted on formation of the vesicle, and is preferably from 5 to 9, and more preferably about 7. The pH can be easily adjusted using a buffer as the solvent in the aqueous solutions. It is advantageous to use the first and second aqueous solutions after adjusting the pH so as to maintain a charged state of a block copolymer and to efficiently form a vesicle.

The temperature of the first and second aqueous solutions is appropriately decided according to solubility of the block copolymers in the solvent, and is preferably from 10 to 80° C., and more preferably from 20 to 60° C.

The ionic strength in the first and second aqueous solutions may be appropriately adjusted so long as an adverse affect is not exerted on formation of the vesicle, and is preferably from 10 to 300 mM, and more preferably from 10 to 150 mM.

In the method of the present invention, a first aqueous solution and a second aqueous solution are mixed. The mixing method is not specifically limited and the second aqueous solution may be added to the first aqueous solution, or the first aqueous solution may be added to the second aqueous solution. Also, the first aqueous solution and the second aqueous solution may be added in a vessel all together and then mixed. The obtained mixed solution of the first aqueous solution and the second aqueous solution may be appropriately stirred.

The temperature at which the first aqueous solution is mixed with the second aqueous solution is not specifically limited so long as an adverse affect is not exerted on formation of the vesicle, and is preferably set taking account of solubility according to the temperature of the block copolymers. The temperature at which mixing is conducted is, for example, from 20 to 50° C.

In the method of the present invention, the mixed solution is allowed to stand to produce a vesicle in the solution. The standing time of the mixed solution varies depending on efficiency of formation of the vesiclem, and is, for example, from 5 to 30 hours.

When a compound is included in the vesicle of the present invention, for example, by adding a compound in a mixed solution containing the first and second block copolymers during formation of a vesicle, the compound can be included in the vesicle. Also, by preliminarily adding a compound to either or both of the first and second aqueous solutions to prepare a mixed solution thereof, the compound can be included in the vesicle. Therefore, the method of the present invention preferably includes a step of adding a compound to be included in the vesicle. In the case of including the compound in the vesicle, operations such as dialysis, dilution, concentration, and stirring can be appropriately added. Also, when the compound is inserted into the membrane of the vesicle, the same technique as described above can be employed.

EXAMPLES

The present invention will now be described in detail by way of examples, but the present invention is not limited to the following examples.

Example 1

1-1: Synthesis of Polyethylene Glycol-Poly(β-Benzyl-L-Aspartate) (PEG-PBLA)

In a 200 ml recovery flask, 250 mg (0.125 mmols) of PEG-NH$_2$ (molecular weight: 2,000) was charged and benzene was added to obtain a solution. This solution was freeze-dried to remove moisture. The atmosphere in the recovery flask was substituted with Ar gas and 5 ml of a mixed solvent (DMF/CH$_2$Cl$_2$=1:4) was added using a syringe to obtain a PEG-NH$_2$ solution. In a separate 100 ml recovery flask, 2.5 g (10.6 mmols: 85 eq) of β-benzyl-L-aspaltate N-carboxylic anhydride (BLA-NCA) was added and also 3 ml of DMF and 50 ml of CH$_2$Cl$_2$ were added to obtain a solution. This solution was added to the recovery flask containing the PEG-NH$_2$ solution using a syringe while stirring. Then, the recovery flask containing the solution was immersed in a constant temperature bath at 35° C. and the solution was reacted while stirring for 2 days. After confirming disappearance of a peak attributed to NCA by IR analysis, about a five-fold amount of ether was added to the reaction solution to obtain a precipitate. This precipitate was filtered and washed several times with ether. Then, the precipitate was freeze-dried using benzene to obtain PEG-PBLA.

With respect to PEG-PBLA, $^1$H NMR measurement was conducted, and then a polymerization degree of BLA was calculated from a proton ratio of an ethylene chain peak of PEG at about 3.5 ppm to a methylene chain peak adjacent to a benzene ring at about 5 ppm and was found to be about 100. GPC measurement was conducted. As a result, the molecular weight distribution was 1.18.

1-2: Synthesis of Polyethylene Glycol-Polyaspartic Acid (PEG-PAsp)

In a 200 ml recovery flask, 300 mg of PEG-PBLA obtained in 1-1 and 5 ml of acetonitrile were charged to obtain a solution. To this solution, 2.5 ml of an aqueous 1N NaOH solution was added, followed by stirring at room temperature for one hour. The resulting reaction solution was charged in a dialysis tube (MWCO 3500) and dialysis was conducted for 3 days using distilled water as an external solution. The external solution was replaced several times and the internal solution was recovered, followed by freeze drying to obtain PEG-PAsp as a white solid.

With respect to PEG-PAsp, $^1$H NMR measurement was conducted, and then a polymerization degree of polyaspartic acid was calculated from a proton ratio of an ethylene chain peak of PEG at about 3.5 ppm to a methylene chain peak of polyaspartic acid at about 2.6 ppm and was found to be about 98. The results revealed that the deprotection reaction of PBLA quantitatively proceeded and the molecular weight was found to be 13,500.

1-3: Synthesis of Aminated Compound (PEG-PeDA) of Polyethylene Glycol-Poly-β-Benzyl-L-Aspartate Using 1,5-Pentanediamine 200 mg of PEG-PBLA was dissolved in benzene in a 200 ml recovery flask and freeze-dried. Then, 8 ml of DMF was added to the recovery flask, followed by stirring, addition of 3.2 ml (0.98 mols) of 1,5-diaminopentane purified by distillation, and further stirring at 40° C. for 2 days. The reaction solution was ice-cooled and 16 ml of a 10% acetic acid solution was added to the solution. Then, this reaction solution was charged in a dialysis tube and dialysis was conducted for 2 days using 0.01 N HCl as an external solution. Furthermore, dialysis was conducted several times using distilled water as an external solution. The internal solution was recovered and freeze-dried to obtain PEG-PeDA as a white solid.

With respect to PEG-PeDA, $^1$H NMR measurement was conducted, and then a polymerization degree of an aminated unit was calculated from a proton ratio of a PEG ethylene chain peak at about 3.5 ppm to a CH$_2$ peak adjacent to a primary amine at about 3 ppm and was found to be about 100. The results revealed that 1,5-diaminopentane was quantitatively introduced into the side chain of aspartic acid and the molecular weight of PEG-PeDA was found to be 21,900.

1-4: Formation of Vesicle Using PEG-PeDA and PEG-PAsp

Using 10 mM Tris/HCl (pH 7.4) as a buffer, the concentration of PEG-PeDA and PEG-PAsp were separately adjusted to 1 mg/ml. These solution was weighed so as to adjust the charge number in the PEG-PeDA solution to the same value as that in the PEG-PAsp solution (PEG-PeDA/PEG-PAsp (w/w)=1.62), and then the respective solutions were filtered through a membrane filter having a pore size of 0.22 μm. The resulting two solutions were mixed, stirred and allowed to stand at room temperature.

1-5: Formation of Vesicle Including FITC-Dextran Therein Using PEG-PeDA and PEG-PAsp Using 10 mM Tris/HCl (pH 7.4) as a buffer, the concentrations of PEG-PeDA and PEG-PAsp were separately adjusted to 1 mg/ml. Dextran having a molecular weight of 42,000 labeled with a fluorescent dye FITC was added and dissolved in a PEG-PAsp solution at a concentration of 1.5 μg/ml. The solutions were weighed so as to adjust the charge number in a PEG-PeDA solution to the same value as that in a PEG-PAsp solution (PEG-PeDA/PEG-PAsp (w/w)=1.62), and then the respective solutions were filtered through a membrane filter having a pore size of 0.22 μm. The resulting two solutions were mixed, stirred and allowed to stand at room temperature.

1-6: Observation Using Dark Field Microscope: Analysis of Vesicle

Figure 2:
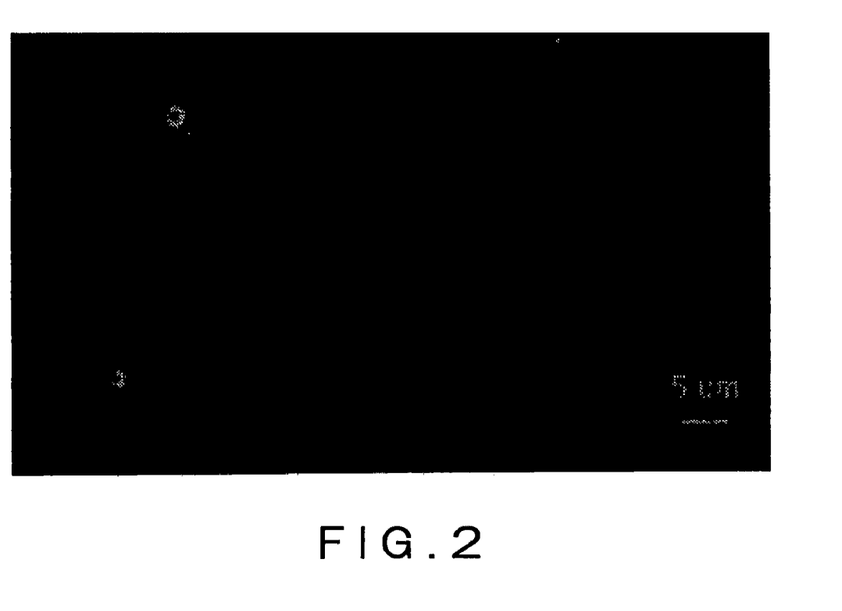
FIG. 2 is a photograph of a vesicle formed of PEG-PeDA and PEG-PAsp observed by a dark field microscope.

The solution obtained in 1-4 was dropped on a slide glass and a cover glass was put thereon, and then observed by a dark field microscope. The results are as shown in FIG. 2. Scattered light due to a spherical aggregate measuring about 1 to 10 μm was observed and the aggregate had a hollow structure.

1-7: Observation Using Confocal Microscope

Figure 3:
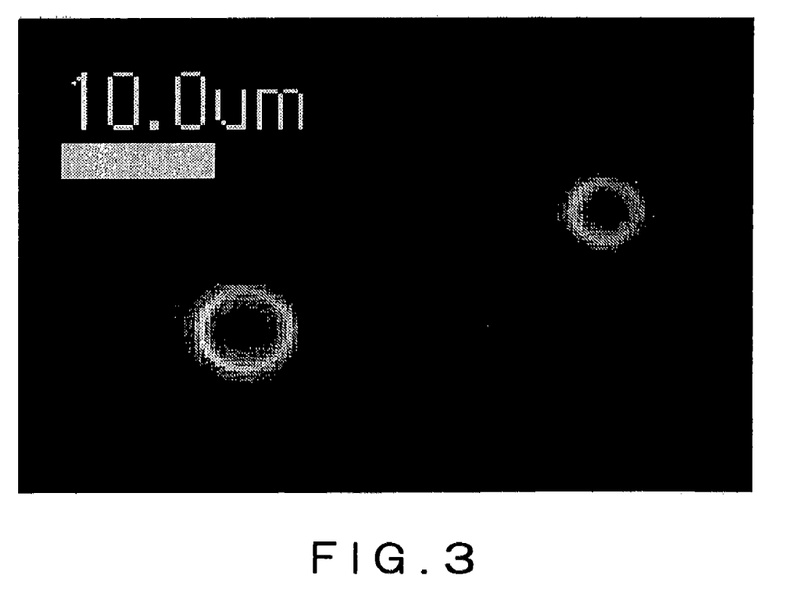
FIG. 3 is a photograph of a vesicle formed of PEG-PeDA and PEG-PAsp observed by a confocal microscope.

The solution obtained in 1-5 was dropped on a glass plate and then observed by a confocal microscope. The results are as shown in FIG. 3. A spherical aggregate about 1 to 10 μm was observed. Furthermore, fluorescence due to FITC was observed in an inner phase of the spherical aggregate. The results revealed that the aggregate has a hollow structure and FITC-dextran exists in the space of an inner aqueous phase.

Example 2

2-1: Synthesis of Poly(2-Isopropyl-2-Oxazoline)-Poly(ε(Benzyloxycarbonyl)-L-Lysine) (PiPrOx-PLys (Z))

20 mg ($0.44 \times 10^{-2}$ mmols) of poly(2-isopropyl-2-oxazoline)-$NH_2$ (PiPrOX—$NH_2$) was weighed in a recovery flask, dissolved in benzene and freeze-dried. Then, the atmosphere in the recovery flask was substituted with Ar and 1 ml of DMF was added. In a separate recovery flask, ε (benzyloxycarbonyl)-L-lysine N-carboxylic anhydride (Lys (Z)-NCA)) was weighed in an amount corresponding to 80 units (107.8 mg, 0.352 mmols) based on PiPrOX—$NH_2$ under Ar and was dissolved by adding DMF (1 ml). Using a syringe, the resulting solution was added to the recovery flask containing PiPrOX—$NH_2$ while stirring. Then, the recovery flask containing the solution was immersed in a constant temperature bath at 37.5° C. and the solution was reacted while stirring for 4 days. After confirming disappearance of a peak attributed to NCA by IR analysis, the reaction solution was added to about a ten-fold amount of hexane to obtain a precipitate. This precipitate was filtered and washed several times with hexane. Then, the precipitate was transferred to the recovery flask, vacuum-dried and then freeze-dried from benzene to obtain PiPrOx-PLys (Z).

With respect to PiPrOx-PLys (Z), $^1$HNMR measurement was conducted, and then a polymerization degree of Lys (Z)-NCA was calculated from a proton ratio of a peak attributed to a methyl group of a PiPrPOx side chain at about 1.0 ppm to a methylene chain peak adjacent to a benzene ring at about 4.9 ppm and found to be about 79. GPC measurement was conducted. As a result, the molecular weight distribution was 1.2.

2-2: Synthesis of Poly(2-Isopropyl-2-Oxazoline)-Poly(L-Lysine) (PiPrOx-P (Lys))

To 100 mg of PiPrOx-PLys (Z) obtained in 2-1, 5 ml of trifluoroacetic acid (TFA) was added, followed by stirring to obtain a solution. To this solution, 10 ml of 30% HBr/AcOH was added, followed by stirring at room temperature for 1.5 hours. The resulting solution was dropped in about a 15-fold amount of hexane to obtain a precipitate. The resulting precipitate was dissolved in water and the solution was charged in a dialysis tube (MWCO 3500) and dialysis was conducted using distilled water as an external solution. The external solution was replaced several times and, after the pH of the external solution became nearly neutral, the internal solution was recovered, followed by freeze drying to obtain PiPrOx-P (Lys).

With respect to PiPrOx-P (Lys), $^1$H NMR measurement was conducted, and then a polymerization degree of Lys was calculated from a proton ratio of a peak attributed to a methyl group of PiPrOx side chain at about 1.0 ppm to a peak attributed to α-methine of Plys at about 4.2 ppm and was found to be about 82.

2-3: Synthesis of Poly(2-Isopropyl-2-Oxazoline)-Poly-β-Benzyl-L-Aspartate (PiPrOx-PBLA)

20 mg ($0.44 \times 10^{-2}$ mmols) of PiPrOX—$NH_2$ was weighed in a recovery flask, dissolved in benzene and then freeze-dried. The atmosphere in the recovery flask was substituted with Ar and 1 ml of $CH_2Cl_2$ was added. In a separate recovery flask, BLA-NCA was weighed in an amount corresponding to 80 units (88 mg, $3.2 \times 10^{-4}$ mol) based on PiPrOX—$NH_2$ under Ar and was dissolved by adding 1 ml of $CH_2Cl_2$. Using a syringe, the resulting solution was added to the recovery flask containing PiPrOX—$NH_2$ while stirring. Then, the recovery flask containing the solution was immersed in a constant temperature bath at 37.5° C. and the solution was reacted while stirring for 3 days. After confirming disappearance of a peak attributed to NCA by IR analysis, the reaction solution was added to about a ten-fold amount of hexane to obtain a precipitate. This precipitate was filtered and washed several times with hexane. Then, the precipitate was transferred to the recovery flask, vacuum-dried and then freeze-dried from benzene to obtain PiPrOx-PBLA.

With respect to PiPrOx-PBLA, $^1$HNMR measurement ($CD_2Cl_2$) was conducted, and then a polymerization degree of BLA-NCA was calculated from a proton ratio of a peak attributed to a methyl group of a PiPrPOx side chain at about 1.0 ppm to a methylene chain peak adjacent to a benzene ring at about 5.1 ppm and was found to be about 80. GPC measurement was conducted. As a result, the molecular weight distribution was 1.1.

2-4: Synthesis of Polyethylene Glycol-Polyaspartic acid (PEG-PAsp)

In the same manner as in 1-2, polyethylene glycol-polyaspartic acid (PEG-PAsp) was obtained.

2-5: Formation of Vesicle Using PiPrOx-P (Lys) and PEG-PAsp

In the same manner as in 1-4, a vesicle was produced using PiPrOX—P (Lys) and PEG-PAsp.

2-6: Observation Using Dark Field Microscope: Analysis of Vesicle

Figure 4:
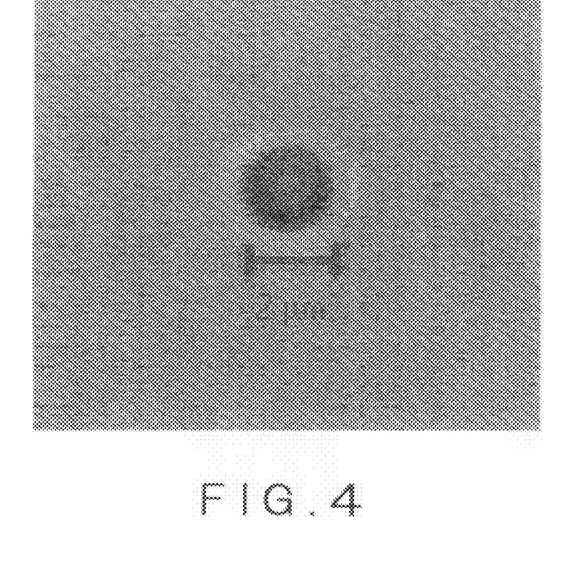
FIG. 4 is a photograph of a vesicle formed of PiPrOX—P (Lys) and PEG-PAsp observed by a dark field microscope.

The solution obtained in 2-5 was dropped on a slide glass and a cover glass was put thereon, and then observed by a dark field microscope. The results are as shown in FIG. 4. A spherical aggregate measuring about 1 to 10 μm existed and the aggregate had a hollow structure.

2-7: Observation Using Transmission Electron Microscope

Figure 5:
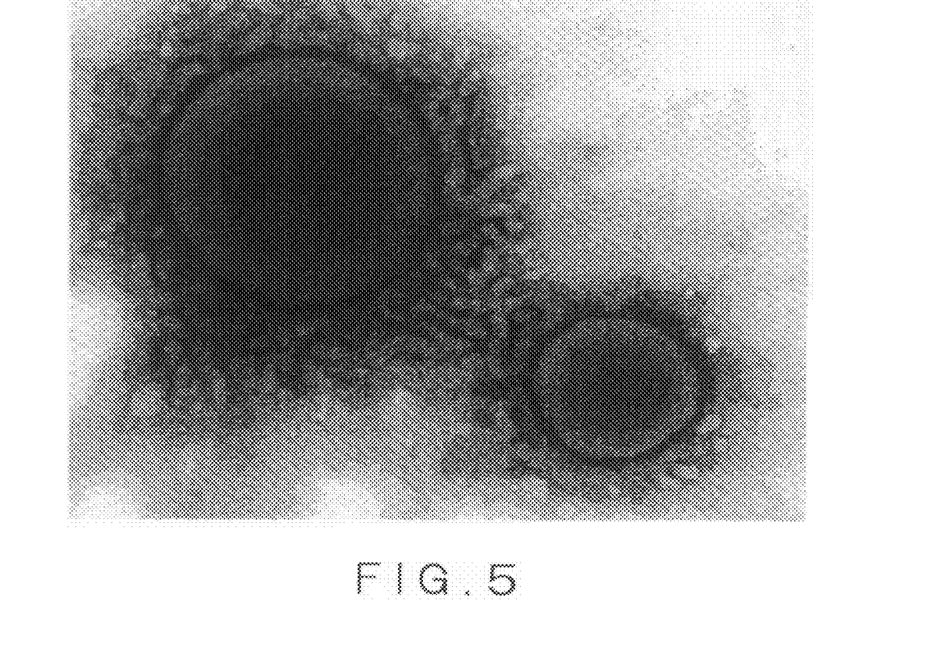
FIG. 5 is a photograph of a vesicle formed of PiPrOx-P (Lys) and PEG-PAsp observed by a transmission electron microscope.

The solution obtained in 2-5 was dropped on a Cu grid on which a Formvar supporting film is spread, and a trace amount of uranium acetate was dropped. Excess moisture was absorbed by a filter paper, followed by drying to obtain a grid. The grid was observed by a transmission electron microscope. The results are as shown in FIG. 5. A spherical aggregate measuring about 100 nm to 10 μm existed and the aggregate had a hollow structure.

Example 3

3-1: Formation of Vesicle Using PEG-PeDA and PEG-PAsp in The Presence of NaCl Having a Saline Concentration Using 10 mM Tris/HCl (pH 7.4) containing 150 mM NaCl having a saline concentration as a buffer, the concentrations of PEG-PeDA and PEG-PAsp were separately adjusted to 1 mg/ml. Dextran having a molecular weight of 42,000 labeled with a fluorescent dye FITC was added and dissolved in the PEG-PAsp solution at a concentration of 1 mg/ml. The solutions were weighed so as to adjust the charge number in the PEG-PeDA solution to the same value as that in a PEG-PAsp solution (PEG-PeDA/PEG-PAsp (w/w)=1.62), and then the respective solutions were filtered through a membrane filter having a pore size of 0.22 µm. The resulting two solutions were mixed, stirred. Further, the solution was applied to ultrasonic treatment for 20 minutes and then allowed to stand at room temperature. Then, this solution was diluted 100-times with a buffer.

3-2: Observation Using Confocal Microscope

Figure 6:
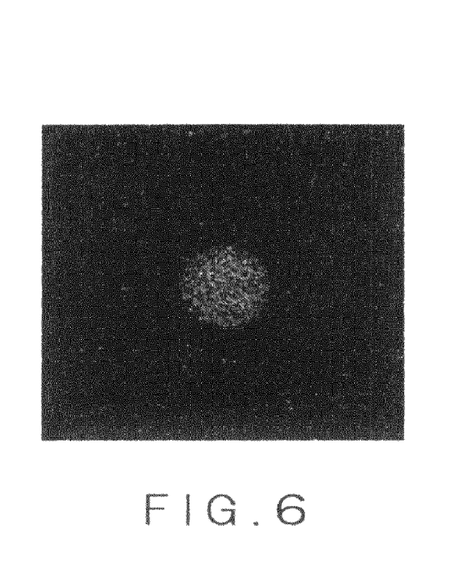
FIG. 6 is a photograph of a vesicle formed of PEG-PeDA and PEG-PAsp in the presence of a saline concentration of NaCl, observed by a confocal microscope.

The solution obtained in 3-1 was dropped on a glass plate, and then observed by a confocal microscope. The results are as shown in FIG. 6. A spherical aggregate measuring about 1 to 10 µm existed. Also, scattered light due to FITC was observed in an inner phase of a spherical aggregate.

Furthermore, the solution was allowed to stand at room temperature for three or more months and then observed by a confocal microscope. As a result, the spherical aggregate maintained the form thereof. The results revealed that the spherical aggregate holds the structure at room temperature in the presence of a colloid osmotic pressure of about 10 µM Osm for three or more months.

Example 4

Confirmation of Permeability of Vesicle Membrane Using Fluorescent Dyes Each Having Different Molecular Weights 4-1: Addition of Vesicle to Fluorescent Dye Solution A fluorescent dye, tetramethyl rhodamine isocyanate (TRITC) having a molecular weight of 443.5 and dextran having a molecular weight of about 70,000 labeled with TRITC were separately dissolved in a buffer of 10 mM Tris/HCl (pH 7.4) containing 150 mM NaCl. Then, 900 µL of each of the two kinds of solutions thus obtained was added to 100 µL of a solution containing a spherical aggregate including FITC obtained in 3-1.

4-2: Observation Using Confocal Microscope

Each of the solutions obtained in 4-1 was dropped on a glass plate and was evaluated by a confocal microscope.

Figure 7:
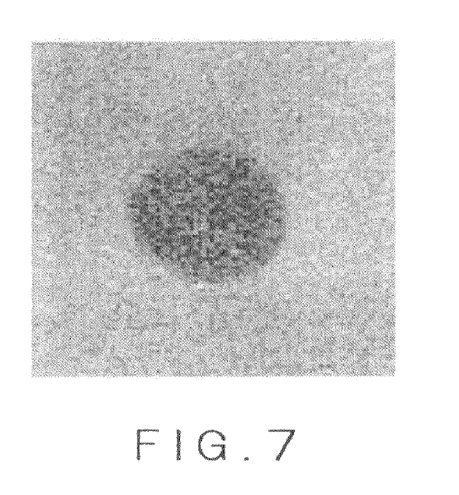
FIG. 7 is a photograph of a vesicle formed of PEG-PeDA and PEG-PAsp, which includes FITC-dextran in the case of adding a solution of dextran labeled with TRITC, observed by a confocal microscope.
Figure 8:
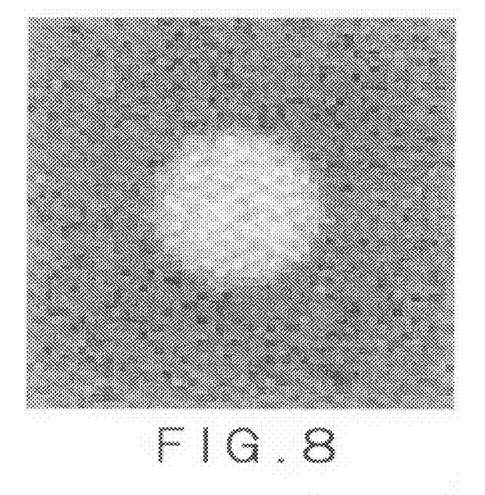
FIG. 8 is a photograph of a vesicle formed of PEG-PeDA and PEG-PAsp, which includes FITC-dextran in the case of adding a solution of TRITC, observed by a confocal microscope.

When a solution of dextran labeled with TRITC was added, an image shown in FIG. 7 was obtained. In FIG. 7, green fluorescent light of FITC was observed in an inner phase of a spherical aggregate, while red fluorescent light of TRITC was observed in an outer phase of a spherical aggregate. In contrast, when a solution of TRITC was added, an image shown in FIG. 8 was obtained. In FIG. 8, yellow fluorescent light which was based on the overlapping of green color of FITC and red color of TRITC was observed in an inner phase of a spherical aggregate.

As shown in FIG. 7 and FIG. 8, dextran labeled with TRITC did not permeate into the inner phase of the spherical aggregate, while TRITC having a lower molecular weight than that of the dextran permeated into the inner phase of the spherical aggregate. Thus, these results revealed that the membrane of the spherical aggregate exhibits semi-permeability.

Example 6

Confirmation of Vesicle Comprising PEG-PeDA and PEG-PAsp in the Presence of Serum 6-1: Preparation of Vesicle and Addition of Serum Using 10 mM Tris/HCl (pH 7.4) containing 150 mM NaCl having a saline concentration as a buffer, the concentration of PEG-PeDA and PEG-PAsp were separately adjusted to 1 mg/ml. The solutions were weighed so as to adjust the charge number in the PEG-PeDA solution to the same value as that in a PEG-PAsp solution (PEG-PeDA/PEG-PAsp (w/w)=1.62). Then, each solution was filtered through a membrane filter having a pore size of 0.22 µm. The resulting two solutions were mixed, stirred and allowed to stand at room temperature. To 90 µL of the mixed solution, 10 µL of fetal bovine serum was added and, after stirring again, the mixture was allowed to stand.

6-2: Observation Using Dark Field Microscope

Figure 9:
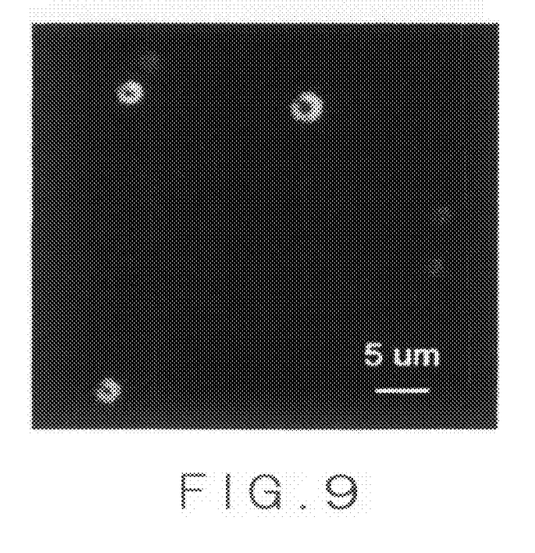
FIG. 9 is a photograph of a vesicle formed of PEG-PeDA and PEG-PAsp in the presence of serum observed by a dark field microscope.

The solution obtained in 6-1 was allowed to stand for one day, dropped on a glass plate and then observed by a dark field microscope. As shown in FIG. 9, a spherical aggregate measuring about 1 to 5 µm existed and the aggregate had a hollow structure. The results revealed that a spherical aggregate holds a hollow structure in a solution in which 10% thereof is serum.

The invention claimed is:

1. A vesicle comprising a membrane which is formed of a first block copolymer containing a non-chargeable hydrophilic segment and a chargeable segment, and a second block copolymer containing a non-chargeable hydrophilic segment and a chargeable segment having an electric charge which is opposite to that of the chargeable segment in the first block copolymer.

2. The vesicle according to claim 1, wherein the membrane has a three-layered structure comprising an outer layer, an intermediate layer and an inner layer, the chargeable segment in the first block copolymer and the chargeable segment in the second block copolymer are bonded through electrostatic interaction to form the intermediate layer, and the non-chargeable hydrophilic segments form the outer layer and the inner layer.

3. The vesicle according to claim 2, wherein the non-chargeable hydrophilic segment in either one of the first block copolymer and the second block copolymer forms the outer layer, and the non-chargeable hydrophilic segment in the other block copolymer, which does not form the outer layer, forms the inner layer.

4. The vesicle according to claim 1, wherein the non-chargeable hydrophilic segment in the first block copolymer and the non-chargeable hydrophilic segment in the second block copolymer are polyethylene glycol and/or poly(2-isopropyl-2-oxazoline).

5. The vesicle according to claim 1, wherein the chargeable segment which is able to be positively charged in the first block copolymer or the second block copolymer is represented by the following formula (I):

(I)

wherein
- $R_1$ represents —$(CH_2)_3NH_2$ group or —$CONH(CH_2)_s$—X, s representing 0 to 20, wherein X represents at least one selected from the group consisting of —$NH_2$, pyridyl, morpholyl, 1-imidazolyl, piperazinyl, 4-($C_{1-6}$ alkyl)-piperazinyl, 4-(amino $C_{1-6}$ alkyl)-piperazinyl, pyrrolidin-1-yl, N-methyl-N-phenylamino, piperidinyl, diisopropylamino, dimethylamino, diethylamino, —$(CH_2)_tNH_2$, and —$(NR_9(CH_2)_o)_pNHR_{10}$ wherein $R_9$ represents hydrogen or methyl, $R_{10}$ represents hydrogen, acetyl, trifluoroacetyl, benzyloxycarbonyl, or tert-butoxycarbonyl, and o represents 1 to 5, p represents 1 to 5, and t represents 0 to 15;
- $R_2$ represents hydrogen, acetyl, trifluoroacetyl, acryloyl, or methacryloyl;
- a represents 0 to 5,000;
- b represents 0 to 5,000; and
- a+b represents 2 to 5,000.

6. The vesicle according to claim 5, wherein $R_1$, represents —$CONH(CH_2)_s$—$NH_2$ and s represents 2 to 5;
- $R_2$ represents a hydrogen atom;
- a represents 0 to 200; b represents 0 to 200; and
- a+b represents 10 to 200.

7. The vesicle according to claim 1, wherein the chargeable segment which is able to be negatively charged in the first block copolymer or the second block copolymer is represented by the following formula (II):

(II)

wherein
- $R_2$ represents hydrogen, acetyl, trifluoroacetyl, acryloyl, or methacryloyl,
- each $R_3$ independently represents methylene or ethylene, and
- c represents 0 to 5,000, d represents 0 to 5,000, and c+d represents 2 to 5,000.

8. The vesicle according to claim 7, wherein $R_2$ represents hydrogen,
- $R_3$ represents methylene, and
- c represents 0 to 200, d represents 0 to 200, and
- c+d represents 10 to 200.

9. The vesicle according to claim 1, wherein the block copolymer containing the chargeable segment which is able to be positively charged is represented by the following formula (III):

(III)

wherein
- $R_1$ represents —$(CH_2)_3NH_2$ or —$CONH(CH_2)_s$—X and s represents 0 to 20 wherein X represents at least one selected from the group consisting of —$NH_2$, pyridyl, morpholyl, 1-imidazolyl, piperazinyl, 4-($C_{1-6}$ alkyl)-piperazinyl, 4-(amino $C_{1-6}$ alkyl)-piperazinyl, pyrrolidin-1-yl, N-methyl-N-phenylamino, piperidinyl, diisopropylamino, dimethylamino, diethylamino, —$(CH_2)_tNH_2$, and —$(NR_9(CH_2)_o)_pNHR_{10}$ wherein $R_9$ represents hydrogen or methyl, $R_{10}$ represents hydrogen, acetyl, trifluoroacetyl, benzyloxycarbonyl, or tert-butoxycarbonyl, and o represents 1 to 5, p represents 1 to 5, and t represents 0 to 15;
- $R_2$ represents hydrogen, acetyl, trifluoroacetyl, acryloyl, or methacryloyl;
- $R_4$ represents hydrogen, or straight-chain or branched $C_{1-12}$ alkyl which may be substituted;
- $R_5$ represents —$(CH_2)_gNH$— and g represents 0 to 5;
- a represents 0 to 5,000, b represents 0 to 5,000, and a+b represents 2 to 5,000; and
- e represents 5 to 2,500.

10. The vesicle according to claim 9, wherein $R_1$, represents —$CONH(CH_2)_s$—$NH_2$ and s represents 2 to 5,
- $R_2$ represents hydrogen,
- $R_4$ represents methyl, and
- a represents 0 to 200, b represents 0 to 200, and
- a+b represents 10 to 200, and
- e represents 10 to 300.

11. The vesicle according to claim 1, wherein the block copolymer containing the chargeable segment which is able to be positively charged is represented by the following formula (IV):

(IV)

wherein
represents —$(CH_2)_3NH_2$ or —$CONH(CH_2)_s$—X, s representing 0 to 20, wherein X is at least one selected from the group consisting of —$NH_2$, pyridyl, morpholyl, 1-imidazolyl, piperazinyl, 4-($C_{1-6}$ alkyl)-piperazinyl, 4-(amino $C_{1-6}$ alkyl)-piperazinyl, pyrrolidin-1-yl, N-methyl-N-phenylamino, piperidinyl, diisopropylamino, dimethylamino, diethylamino, —$(CH_2)_tNH_2$, and —$(NR_9(CH_2)_o)_pNHR_{10}$ wherein $R_9$ represents hydrogen or methyl, $R_{10}$ represents hydrogen, acetyl, trifluoroacetyl, benzyloxycarbonyl, or tert-butoxycarbonyl, and o represents 1 to 5, p represents 1 to 5, and t represents 0 to 15;

$R_2$ represents hydrogen, acetyl, trifluoroacetyl, acryloyl, or a methacryloyl;

$R_6$ represents hydrogen, or straight-chain or branched $C_{1-12}$ alkyl which may be substituted;

$R_7$ represents —$(CH_2)_h NH$— and h represents 0 to 5;

$R_8$ represents straight-chain or branched $C_{1-12}$ alkyl;

a represents 0 to 5,000, b represents 0 to 5,000 and a+b represents 2 to 5,000; and f represents 5 to 2,500.

12. The vesicle according to claim 11, wherein $R_1$, represents —$(CH_2)_3 NH_2$, $R_2$ represents hydrogen, $R_6$ represents methyl, $R_8$ represents —$CH(CH_3)_2$, a represents 0 to 200, b represents 0 to 200 and a+b represents 10 to 200, and f represents 10 to 300.

13. The vesicle according to claim 1, wherein the block copolymer containing the chargeable segment which is able to be negatively charged is represented by the following formula (V):

[Chemical formula 5]

$$R_4\!-\!\!\left(OCH_2CH_2\right)_{\!i}\!-\!R_5\!-\!\!\left(COCHNH\right)_{\!c}\!-\!\left(COR_3CHNH\right)_{\!d}\!-\!R_2$$
with side chains: $R_3$, $CO$, $OH$ (on the c segment) and $CO$, $OH$ (on the d segment)

(V)

wherein $R_2$ represents hydrogen, acetyl, trifluoroacetyl, acryloyl, or a methacryloyl;

each $R_3$ independently represents methylene or ethylene;

$R_4$ represents hydrogen, or straight-chain or branched $C_{1-12}$ alkyl which may be substituted, $R_5$ represents —$(CH_2)_g NH$— and g represents 0 to 5, c represents 0 to 5,000, d represents 0 to 5,000 and c+d represents 2 to 5,000, and i represents 5 to 2,500.

14. The vesicle according to claim 1, wherein $R_2$ represents hydrogen, $R_3$ represents methylene, $R_4$ represents methyl, c represents 0 to 200, d represents 0 to 200 and c+d represents 10 to 200, and i represents 10 to 300.

15. The vesicle according to claim 1, wherein the block copolymer containing the chargeable segment which is able to be negatively charged is represented by the following formula (VI):

[Chemical formula 6]

$$R_6\!-\!\!\left(NCH_2CH_2\right)_{\!j}\!-\!R_7\!-\!\!\left(COCHNH\right)_{\!c}\!-\!\left(COR_3CHNH\right)_{\!d}\!-\!R_2$$
with side chains: $CO$, $R_8$ (on the j segment); $R_3$, $CO$, $OH$ (on the c segment); $CO$, $OH$ (on the d segment)

(VI)

wherein $R_2$ represents hydrogen, acetyl, trifluoroacetyl, acryloyl, or methacryloyl;

each $R_3$ independently represents methylene or ethylene;

$R_6$ represents hydrogen, or straight-chain or branched $C_{1-12}$ alkyl which may be substituted;

$R_7$ represents —$(CH_2)_h NH$— and h represents 0 to 5, $R_8$ represents straight-chain or branched $C_{1-12}$ alkyl;

c represents 0 to 5,000, d represents 0 to 5,000 and c+d represents 2 to 5,000; and j represents 5 to 2,500.

16. The vesicle according to claim 15, wherein $R_2$ represents hydrogen, $R_3$ represents methylene, $R_6$ represents methyl, $R_8$ represents —$CH(CH_3)_2$, c represents 0 to 200, d represents 0 to 200 and c+d represents 10 to 200, and j represents 10 to 300.

17. The vesicle according to claim 1, wherein the first block copolymer is a block copolymer represented by formula (III) and the second block copolymer is a block copolymer represented by formula (V).

18. The vesicle according to claim 1, wherein the first block copolymer is a block copolymer represented by formula (IV) and the second block copolymer is a block copolymer represented by formula (V).

19. The vesicle according to claim 1, wherein the first block copolymer is a block copolymer represented by formula (III) and the second block copolymer is a block copolymer represented by formula (VI).

20. The vesicle according to claim 1, wherein the first block copolymer is a block copolymer represented by formula (IV) and the second block copolymer is a block copolymer represented by formula (VI).

21. The vesicle according to claim 1, wherein a compound is contained within a center void of the vesicle.

* * * * *